United States Patent [19]

Goldstein

[11] 4,415,660

[45] Nov. 15, 1983

[54] METHOD OF MAKING A CLONING VECTOR

[75] Inventor: Richard N. Goldstein, Cambridge, Mass.

[73] Assignee: President and Fellows of Harvard College, Cambridge, Mass.

[21] Appl. No.: 357,414

[22] Filed: Mar. 12, 1982

Related U.S. Application Data

[62] Division of Ser. No. 881,170, Feb. 27, 1978, Pat. No. 4,332,901.

[51] Int. Cl.³ ............................................ C12N 15/00
[52] U.S. Cl. .................................................. 435/172
[58] Field of Search ....................... 435/172, 235, 317

[56] References Cited

PUBLICATIONS

Gibbs et al., Virology, vol. 53, pp. 24–39 (1973).
Lamanna et al., The Williams & Wilkins Co., pp. 723–727 (1965).
Metzler, Biochemistry, The Chemical Reactions of Living Cells, pp. 945–946.
Garland et al., Biochemistry of Genetic Engineering (1979).

*Primary Examiner*—Alvin E. Tanenholtz

[57] ABSTRACT

A cloning vector useful in recombining DNA (i.e. recombinant DNA studies) is made by mutagenesis of a satellite bacteriophage P4 wt or P4 vir$_1$ and subsequent separation and purification of the mutant progeny in a cesium chloride equilibrium density gradient. On such a cesium chloride gradient the mutant is found in a range of densities from 1.35 to 1.42 g/ml at 24° C. with peaks at about 1.42, 1.39, and 1.35 g/ml.

5 Claims, 1 Drawing Figure

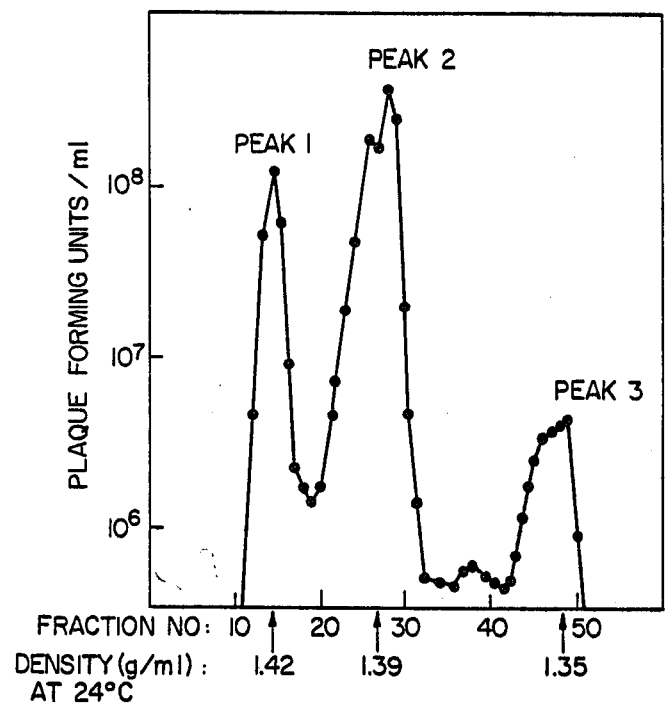

METHOD OF MAKING A CLONING VECTOR

This is a division, of application Ser. No. 881,170, filed Feb. 27, 1978 now U.S. Pat. No. 4,332,901.

The invention described herein was made in the course of work under a grant or award from the Department of Health, Education and Welfare.

This invention relates to a cloning vector for use in replicating foreign DNA segments and in producing gene products (proteins) coded for by these segments and to the method of making such a vector. The vector is useful in cloning segments of genes to produce antibodies for making vaccines; it is also useful in cloning in bacteria DNA obtained from animals to provide animal proteins such as hormones.

Plasmids (extrachromosomal DNA elements) and bacteriophage (bacterial viruses) have previously been proposed and subsequently certified by the National Institutes of Health for use as vectors in recombinant DNA procedures. Both types of vectors are capable of infecting a bacterial host while carrying along with it a new recombinant segment of DNA. Such known vectors possess a variety of characteristics affecting their safety, i.e., the ease and effectiveness of achieving vectors biological containment. In particular, phage vectors seem to be nonmobilizable—i.e., they will not be transferred via bacterial transduction (mating) of the host bacteria of other bacteria in the environment. They also do not seem to carry antibiotic resistance as frequently as plasmids. And, most important, their genetics is far better understood, allowing for the construction of various mutations in essential control genes. In turn, this control allows for genetic manipulation of the development of the virus therefore enhancing the potential for biological containment. However, they suffer from the disadvantage that both the phage DNA and the added recombinant DNA must be encapsidated within the phage capsid which is of limited capacity.

On the other hand, plasmids are able to carry much larger segments of foreign DNA (genes) than can be carried by bacteriophage since there is no requirement, as there is for bacteriophage, for encapsidation of the DNA within a bacteriophage capsid of defined (i.e. limited) capacity. In addition, it has also proven possible to amplify (i.e. greatly increase) the amount of plasmid DNA within the bacterial host by adopting conditions which block bacterial DNA replication while allowing plasmid DNA replication to continue at a high rate. The result of such amplification of the plasmid DNA results also in amplification of the additional extraplasmid DNA of interest which has been inserted into the plasmid. Despite these advantages, plasmids have been criticized for use in recombinant DNA processes because of their ubiquitous nature, the ease with which they can be transferred to unrelated bacterial hosts, and their will known association with antibiotic resistance.

The cloning vector of the present invention, a satellite bacteriophage identified as P4 $sid_1$, a size determination mutant of P4 wt (wt=wild type), or of P4 $vir_1$, an immunity-insensitive clear plaque mutant which is a derivative of P4 wt, possesses a unique combination of characteristics and properties making it superior in utility and in safety to previously known vectors, both plasmid and bacteriophage. It has the ability to be grown and maintained either as a plasmid or a bacteriophage. The control over either of its lift styles is easily accessible through a series of amber and temperature sensitive genetic mutations. As a satellite bacteriophage, the correction of its defectiveness is under the control of its helper bacteriophage P2. This then acts as a double 'fail-safe' system, since another large series of amber, temperature sensitive, and deletion mutations exist in the helper bacteriophage which can all be used to control and regulate the growth of P4 $sid_1$.

The P4 $sid_1$ vector also surpasses any other known bacteriophage vector system in the amount of additional genetic information which it can carry and clone due to its large volume capsid. Although P4 wt and P4 $vir_1$ both have small volume capsids with a diameter of $455\pm15$ Å, the P4 mutant of the present invention, which maps in the P4 sid gene, is one whose expression results in progeny more than 99% of which have large capsids of substantially the same size at the larger helper P2 capsids, that is, capsids having a diameter of $595\pm30$ Å. The functional utility resulting from the large volume capsid also provides increased safety as to biological containment because fewer and smaller volume procedures are required to clone a given series of recombinant DNA fragments. Most importantly, it does not suffer from an inherent association with antibiotic resistance factors as do many plasmids. This again results in increased safety because there will be no such positive selective factors for its survival it it is inadvertently carried out of the environment of containment.

Finally, with respect to increased safety, the P4 sid vector has a rigid requirement for calcium ion for adsorption and magnesium ion for stability. It also survives poorly outside of a host cell unless kept well below room temperature. Such restrictions on its growth and stability again facilitate biological containment.

In summary, the features of the satellite bacteriophage P4 $sid_1$ vector of the present invention are:

a. it is a defective bacterial virus which depends for its lytic multiplication on at least 18 genes of a helper bacteriophage such as P2, in addition to depending on various host cell functions;

b. it can carry for more heterologous DNA (i.e. non-P4 DNA) than other bacteriphage vectors so developed for recombinant DNA procedures. It is believed that it can carrry somewhere between $14\times10^6$ to $18\times10^6$ daltons of non-P4 DNA;

c. it is mutated in the function(s) responsible for direction (determination) of the normally small size satellite P4 capsid and as such results in the production of a capsid having a volume approximately three times as great as that of P4 wt; and d. it can be replicated either as a plasmid or as a bacteriophage; in the former state it is believed that it can be amplified while in the latter state it can be replicated lytically by rescue with a helper bacteriophage.

The features facilitating biological containment of the vector are:

a. it has an essential requirement for at least 18 genes of a helper bacteriophage for lytic growth; it also has essential requirements for various bacterial host functions;

b. numerous amber, temperature sensitive, and deletion mutants which exist in P2 and P4 bacteriophages can be used to control all essential functions such as DNA replication, assembly, and packaging; host cell functions can also be used to control its growth;

c. it has stringent requirements for magnesium ion for stability and calcium ion for adsorption;

d. it survives poorly at room temperature and must be stored in the cold;

e. a virulent mutation, called vir$_1$, greatly reduces the probability that it will integrate (lysogenize) the host chromosome;

f. though it can be grown either as a plasmid or a bacteriophage it can be stored in the latter state, so that all clones can be easily concentrated and purified as bacteriophage while all host cells can be destroyed after use;

g. host cells to be used for experimentation can be first tested easily for contamination by helper bacteriophage required for lytic growth of the P4 sid$_1$ vector (and any clone which it may carry);

h. it is believed that it could be amplified as a plasmid thereby allowing for production of large quantities of the cloned fragment of DNA in batch procedures smaller in volume and fewer in number than the case of previously known phage vectors; and i. it is not normally associated with antibiotic resistance factors or any other known factors which might give it a positive survival factor if carried outside of the environment of containment.

The cloning vector of the present invention is made by mutagenizing a strain of bacteriophage known as P4 wt or P4 vir$_1$, preferably by ultraviolet radiation, followed by separation of the mutant progeny in a cesium chloride density gradient. In such an equilibrium gradient P4 sid$_1$ type mutant progeny will be found through the range of densities from that of normal P4 wt to that of P2 wt, that is from about 1.35 to 1.42 g/ml at 24° C. Within this range there will be peaks of P4 sid$_1$ plaque forming units at about 1.35 and 1.39 and/or 1.42 g/ml respectively. The portion forming the heaviest density peak, accounting for approximately 19% of the mutant vector progeny produced, has a capsid diameter identical to that of the large capsid of helper phage P2; the portion forming the intermediate density peak, accounting for approximately 80% of the mutant vector progeny produced, also has a capsid diameter identical to that of helper phage P2 wt. Less that one percent of the total progeny vector produced by the process of the present invention displays a cesium chloride density of plaque forming units peaking at about 1.35 g/ml, the same density as P4 wt phage, and having a capsid of the same small diameter as that of P4 wt. Moreover, even this small fraction of the mutant which displays a peak of plaque forming units at the same density of cesium chloride as P4 wt and which has the same size capsid as P4 wt differs from the latter in that the progeny produced by the P4 sid$_1$ phage of this fraction have predominantly (i.e., over 99%) large capsids of substantially the same size as P2. In other words, the P4 sid$_1$ of P4 wt density still contain the genetic mutation which will result in the production of large size capsids. The relative capsid sizes are confirmed by electron microscopy showing the vector displaying density peaks of plaque forming units at 1.42 and 1.39 g/ml to have a capsid diameter of 595±30 Å, while that showing density of 1.35 g/ml has a capsid diameter of 455±15 Å. The vector made by the process of the present invention also gives tiny plaques and low bursts under standard non-permissive conditions (su$^-$ or 42° C.) indicating a smaller burst than normal P4 wt phage. These vector phenotypes and the capsid size phenotype are also expressed at temperatures of 30°, 37°, and 42° C. and in both the presence and the absence of the sup D and sup F amber suppressors.

The large diameter capsid of the cloning vector of the present invention can contain up to three copies of its genome. Since only one genome is required for replication, and since 80% of the progeny vector produced (the portion displaying plaque forming unit density peaking at 1.39 g/ml) contains two copies of its genome and 19% (the portion displaying a density peak at 1.42 g/ml) contains three copies, it is apparent that the additional large non-essential or repetitive segments of DNA can be replaced by a segment of foreign DNA of equal size (up to at least $14 \times 10^6$ daltons) but of different coding specificity. This replacement can be done by recombination and/or transposition, or by restriction enzyme procedures as described by Hamer et al., Proc. Nat. Acad. Sci. USA 73, 1537–1541 (1976).

A culture of the novel bacteriophage cloning vector of the present invention, P4 sid$_1$, has been deposited with American Type Culture Collection, 12301 Parklawn Drive, Rockville, Md. and is available at ATCC No. 29746-B1. In addition, a culture of P4 wt from which the cloning vector of the present invention can be made has been deposited in the same location and is available as ATCC No. 29745-B1. Two lysogenic cultures of helper bacteriophage P2, called C339 and C1197, which can serve as host for the P4 sid$_1$ are also available from the same source as ATCC Nos. 29745 and 29746 respectively.

In the drawing, the FIGURE is a plot showing the cesium chloride equilibrium density gradient profile of plaque forming units from the cloning vector made by the process of the present invention.

EXAMPLE

A modified L.B. broth was prepared by first making the following solution:

Bacto tryptone—10 g
Yeast extract–5 g
Sodium chloride—5.8 g
Distilled deionized water, q.s. to make 1 liter The solution was autoclaved for 30 minutes, cooled to room temperature, and the following sterile aqueous solutions were mixed with it:

25% wt/vol sodium chloride—16.8 ml
One molar magnesium chloride—1.6 ml
0.5 Molar calcium chloride—2.0 ml
40% wt/vol glycose—10 ml Tne milliliters of an overnight culture of host (C339 or C119F) bacterium, a P2 lysogen of E. coli strain C-1a was inoculated into 400 ml of modified L. B. broth prepared as described above. The culture was grown to an OD$_{600}$ of 0.1 at 37° C. with aeration. At this time the culture was inoculated with bacteriophage P4 wt (ATCC No. 29745-B1) at an moi (multiplicity of infection) of 0.05. The OD$_{600}$ was monitored periodically, and when growth ceased being logarithmic, ethylene diamine tetraacetic acid sodium salt was added to 2 mM in order to block phage readsorption (both P2 and P4 require calcium ion for adsorption). Aeration was continued for an additional one-half hour until lysis was complete. This protocol allows for two rounds of phage growth. Upon lysis the culture was brought to 3% sodium chloride and 5% polyethylene glycol and centrifuged for forty minutes at 10,000 g. The supernatant was poured off and the pellet was resuspended in 4 ml of "P4 buffer" containing 1% by weight ammonium acetate, 0.08 M magnesium chloride, and 0.01 M Tris hydrochloride (pH 6.8–7.2) in deionized distilled water. One ml of chloroform was then added, and the mixture was briefly vortexed and subsequently spun in a refrigerated clinical centrifuge for 15 minutes. Under these conditions, the phage separated from the cellular debris, forming a top layer above the cellular debris and the bottom layer of chloroform, and could be drawn off with a pasteur pipette. This product contained $10^9$–$10^{10}$ P4 wt phage/ml. The phage was dialyzed against P4 buffer in the cold with three changes of buffer during a 24 hour period.

Phage amounting to $10^8$ P4 wt prepared as described above were mutagenized by irradiation with ultraviolet light by diluting in P4 buffer and exposing to ultraviolet light at 24 erg per mm$^2$ per second to a survival frequency of $10^{-6}$.

A culture of a derivative of E. coli strain C-1a identified as C339 (P2 lysogenic su+ ATCC No. 29745) host was irradiated under the same intensity conditions with ultraviolet light to give a surviving fraction of $5 \times 10^{-2}$. This irradiated P2 lysogenic host, when used to grow the mutagenized P4 wt, produced more mutant progeny than did P2 lysogenic host which had not been thus irradiated, and is consequently preferred as host instead of the latter. Infection of the irradiated P2 lysogenic cells with the irradiated phage was carried out at low moi (0.05) so that the cells were singly infected. Mutants were then allowed to segregate for about 90 min. by growing through one cycle at B 30° C.

The potential mutant phage to be assayed or analyzed were first dialyzed overnight against 500 volumes of cold P4 buffer to remove any chloroform remaining after polyethylene glycol concentration of the lysate. Five milliliters of phage from a single small plaque or the complete mixture of all the mutagenized phage are then adjusted to the appropriate density by the addition of solid cesium chloride. Centrifugation was carried out, optimal separation of particles in each fraction usually being obtained at a speed of 24,000 rpm for 24–36 hrs. at 4° C. After centrifugation and collection of gradient fractions, the desired fractions are plated on any appropriate bacterial indicator host.

Each putative P4 sid mutant small plaque from non-P4 density can be separately regrown and subsequently reassayed via cesium chloride gradient analysis to purify and identify the mutants showing the desired peaks. The desired cloning vector P4 $sid_1$ is found in the range of densities from 1.35 to 1.42 g/ml at 24° C., with over 99% of the plaque forming units forming three peaks, at 1.35, 1.39, and 1.42 g/ml respectively as shown in the drawing.

It is found that even when the fractions having the density of peak 1 or peak 2 or peak 3 as shown in the drawing are isolated from all of the others, upon further growth they spontaneously give rise to the original phenotype showing distribution of densities in the three peaks illustrated, the relative proportions also being approximately the same (after multi-cycle growth) namely, less than 1% exhibiting a density of about 1.35, about 80% peaking at 1.39, and about 19% peaking at 1.42. The mutated cloning vector can be grown in the same type of host baceterium cells, (i.e., ATCC No. 29745 or No. 29746) as the parent. The biologically pure mutant P4 $sid_1$ consequently consists of plaque forming units which appear, in a cesium chloride equilibrium density gradient at 24° C., in the density range from 1.42 to 1.35 g/ml and display a density profile of plaque forming units usually having three peaks at about 1.42, 1.39, and 1.35 g/ml respectively. The plaque forming units or progeny obtained by further growth in a P2 lysogenic culture are distributed non-uniformly among the three peaks, approximately 19% appearing in the first peak (1.42 g/ml), approximately 80% in the second peak (1.39 g/ml) and less than 1% in the third peak (1.35 g/ml). The capsid diameter of those in the first two peaks, amounting to more than 99% of the total, is $595 \pm 30$ Å, identical to that of helper phage P2, while the remainder, less than 1%, have a capsid diameter of $455 \pm 15$ Å, the same as that of P4 wt. The novel cloning vector, as well as its parent phage P4 wt can be stored in P4 buffer at 2°–5° C. but should not be frozen.

SDS polyacrylamide gel electrophoresis shows the cloning vector or phage (P4 $sid_1$) of the present invention to have a protein capsid different from both P2 wt and P4 wt with respect to the species and ratios of cleavage products which arise during cleavage and processing of the major capsid protein.

What is claimed is:

1. A method of making a cloning vector which comprises mutagenizing bacteriophage P4 wt or P4 $vir_1$, then isolating the mutant having plaque forming units appearing, in a cesium chloride equilibrium density gradient at 24° C., in the density range from 1.42 to 1.35 g/ml and displaying a density profile of plaque forming units having three peaks at about 1.42, 1.39 and 1.35 g/ml respectively.

2. A method as claimed in claim 1 in which mutagenizing is carried out by exposing to ultraviolet radiation.

3. A method as claimed in claim 2 in which the ultraviolet radiation is continued to a survival frequency of $10^{-6}$.

4. The method as claimed in claim 1 in which more than 99% of the plaque forming units appear under the peaks at about 1.42 and 1.39 g/ml and the remainder appears under the peak at about 1.35 g/ml.

5. The method as claimed in claim 4 in which more than 99% of the plaque forming units have capsid diameters of $595 \pm 30$ Å and the remainder have a capsid diameter of $455 \pm 15$ Å.

* * * * *

UNITED STATES PATENT AND TRADEMARK OFFICE
CERTIFICATE OF CORRECTION

PATENT NO. : 4,415,660
DATED : November 15, 1983
INVENTOR(S) : Richard N. Goldstein It is certified that error appears in the above—identified patent and that said Letters Patent is hereby corrected as shown below:

Col. 1, line 29, "of other bacteria" should be --to other bacteria--;

Col. 1, line 67, "lift styles" should be --life styles--;

Col. 2, line 16, "at the larger" should be --as the larger--;

Col. 2, line 42, "for more" should be --far more;

Col. 2, line 43, "bacteriophage" is misspelled;

Col. 3, line 18, "than the case of" should be --than in the case of--;

Col. 4, line 44, "One molar" should be --One Molar--;

Col. 4, line 47, "Ten" is misspelled;

Col. 5, line 27, delete "B".

Signed and Sealed this

Thirty-first Day of January 1984

[SEAL]

Attest:

GERALD J. MOSSINGHOFF

Attesting Officer  Commissioner of Patents and Trademarks